United States Patent
Wang et al.

(10) Patent No.: US 9,212,116 B2
(45) Date of Patent: Dec. 15, 2015

(54) METHOD FOR PRODUCING CRESOL FROM PHENOL AND METHANOL VIA GAS PHASE ALKYLATION

(75) Inventors: Kunyuan Wang, Liaoning (CN); Yunpeng Xu, Liaoning (CN); Zhongmin Liu, Liaoning (CN)

(73) Assignee: Dalian Institute of Chemical Physics, Chinese Academy of Sciences, Liaoning (CN)

( * ) Notice: Subject to any disclaimer, the term of this patent is extended or adjusted under 35 U.S.C. 154(b) by 0 days.

(21) Appl. No.: 14/416,209

(22) PCT Filed: Jul. 24, 2012

(86) PCT No.: PCT/CN2012/079082
§ 371 (c)(1),
(2), (4) Date: Jan. 21, 2015

(87) PCT Pub. No.: WO2014/015476
PCT Pub. Date: Jan. 30, 2014

(65) Prior Publication Data
US 2015/0203425 A1    Jul. 23, 2015

(51) Int. Cl.
*C07C 37/11* (2006.01)
*C07C 37/16* (2006.01)
*B01J 29/00* (2006.01)
*B01J 29/40* (2006.01)
*B01J 29/70* (2006.01)

(52) U.S. Cl.
CPC .............. *C07C 37/11* (2013.01); *B01J 29/00* (2013.01); *B01J 29/40* (2013.01); *B01J 29/7007* (2013.01); *B01J 29/7038* (2013.01); *C07C 37/16* (2013.01); *B01J 2229/42* (2013.01)

(58) Field of Classification Search
CPC .................................. C07C 37/11; C07C 37/16
See application file for complete search history.

(56) References Cited

U.S. PATENT DOCUMENTS 4,927,979 A * 5/1990 Yamagishi et al. ........... 568/791

OTHER PUBLICATIONS

Chinese Office Action dated Oct. 8, 2014 issued in corresponding Chinese Application No. 201210258314.2.
Study on the Alkylation of Phenol with Methanol over Zeolite β, Chinese Journal of Catalysis, vol. 19, No. 5, Sep. 1998.
Study on Methylation of Phenol with Methanol over HZSM-5 Zeolite, Chinese Journal of Catalysis, vol. 22, No. 6, Nov. 2001.
Selective synthesis of p-cresol by methylation of phenol, Applied Catalysis A: General, vol. 342, pp. 40-48, 2008.
Study of the phenol methylation mechanism on zeolites HBEA, HZSM5 and HMCM22, Journal of Molecular Catalysis A: Chemical, vol. 327, pp. 63-72, 2010.
Synthesis of cresols by alkylation of phenol with methanol on solid acids, Catalysis Today, vol. 133-135, pp. 720-728, 2008.

* cited by examiner

*Primary Examiner* — Brian J Davis
(74) *Attorney, Agent, or Firm* — Nath, Goldberg & Mayer; Joshua B. Goldberg

(57) ABSTRACT

The present invention relates to a method for producing cresol from phenol and methanol via gas phase alkylation, in which phenol and methanol are preheated and mixed with diluent gas, then the mixture continuously go through a catalyst bed comprising the catalyst for alkylation of phenol with methanol, to produce cresol by gas phase reaction at the reaction temperature of 200~500° C. and the weight hourly space velocity of 0.5~20 $h^{-1}$. The catalyst for alkylation of phenol with methanol is obtained by modification steps and using ZSM-5 zeolite, MCM-22 zeolite or Beta zeolite as an active composition. Using phenol and methanol as feedstock, the cresol selectivity can reach to 90%, and the p-cresol selectivity can reach to 58%. The catalyst is environmental friendly and non-corrosive to the equipment with a good stability and a broad prospect in industrial application.

11 Claims, No Drawings

METHOD FOR PRODUCING CRESOL FROM PHENOL AND METHANOL VIA GAS PHASE ALKYLATION

This is a National Phase Application filed under 35 U.S.C. 371 as a national stage of PCT/CN2012/079082, filed Jul. 24, 2012, the content of which is hereby incorporated by reference in its entirety.

TECHNICAL FIELD

The present invention relates to a method for producing cresol, and particularly relates to a method for producing cresol from phenol and methanol via gas phase alkylation.

BACKGROUND

P-cresol is a colorless liquid or crystal with special odor, which is corrosive and toxic. It is insoluble in water and soluble in alkaline solution or organic solvent, such as toluene, ethanol and so on. P-cresol is an important fine chemical feedstock, which is widely used in many industries, such as antioxidant, dye, medicine, pesticide, spice and so on. O-cresol, also known as 2-cresol, is the important fine chemicals intermediate in synthesis of pesticide, medicine, dye, synthetic resin, spice and antioxidant and so on. M-cresol, also known as 3-cresol, meta-cresol or m-methylphenol, is used mainly as pesticide intermediates to produce insecticide such as fenitrothion, fenthion, MTMC, permethrin. M-cresol is also used as intermediates for producing color film, resin, plasticizer and spices. Coal tar phenol contains approximately 30% of phenol, from 10% to 13% range of o-cresol, from 14% to 18% range of m-cresol, from 9% to 12% range of p-cresol and from 13% to 15% range of xylenol. Natural product separation method was used in the traditional process for producing cresol, and the three isomers of cresol can be recycled.

Due to the limitation of resources and the complex process with numerous separating equipments in the traditional process, chemical synthesis processes for cresol are developed after years of efforts and exploration. Since the success of chemical synthesis, the production equipment for cresol preparation via natural product separation is closed one after another. Nearly ten kinds of chemical synthetic routes have been reported.

Toluene sulfonated alkali fusion method is the traditional synthetic production technology for cresol. Toluene is sulfonated into toluenesulfonic acid, and then sodium hydroxide is used to treat molten sulfonated bodies to obtain cresol sodium salt. Sodium salt is mixed with water, into which sulfur dioxide or sulfuric acid is introduced for acidification to obtain cresol. Composition and content of cresol isomer depend on the reaction conditions, in which p-cresol is the main product and sulfonating agent could select from sulfuric acid or chlorosulfonic acid. Usually, alkali is sulfonated by sulfuric acid at the reaction temperature of 110° C., the product composing from 5% to 8% range of o-cresol and m-cresol, from 84% to 86% range of p-cresol and the dimethyl phenol; when chlorosulfonic acid used to sulfonate alkali at the reaction temperature of 40° C., the product compose from 84% to 86% range of p-cresol, from 14% to 16% range of o-cresol, without m-cresol. This method is mature, simple and suitable for the production of p-cresol. But usage of a large amount of strong acid and alkali bring the corrosion to equipment and serious pollution to environment, and the intermittent production mode is suitable for small-scale production. At present, it is the main method for producing p-cresol in China.

Toluene chlorination-hydrolysis method is cresol mixture obtained from toluene by chlorination substitution in benzene ring and hydrolyzation. Firstly, toluene contacts with chlorine gas at 230° C. in reactor to obtain the mixture of three kinds of chlorotoluene on the Cu—Fe catalyst. Secondly, the mixture is hydrolyzed to obtain cresyl sodium salt mixture at 425° C. on the catalyst $SiO_2$. The hydrolysis reaction is continuous. The cresyl sodium salt solution is acidified and neutralized to obtain cresol mixture, which is separated by distillation to obtain p-cresol, o-cresol and m-cresol. The rate of m-cresol, o-cresol to p-cresol is 1:2:1. The method causes environmental pollution and the low quality product with lots of by-products.

Phenol alkylation method is production of o-cresol from phenol using methanol as alkylating agent. In the liquid phase condition, phenol reacts with methanol via methylation to obtain o-cresol on the $Al_2O_3$ catalyst, at the temperature from 300° C. to 400° C. and the pressure from 1 MPa to 3 MPa. The product comprises from 43% to 51% range of o-cresol, from 17% to 36% range of m-cresol and from 17% to 36% range of p-cresol. But comparing to other synthetic routes of mixed cresol, the method is uncompetitive due to the harsh reaction condition and lots of impurities in product.

Isopropyltoluene method is that isopropyl toluene is converted into methyl isopropyl benzene hydroperoxide under the initiation of peroxide free radical of hydrogen, and then oxidized by oxygen in air. Similar to the oxidization process of cumene to phenol and acetone, the products are rich in m-cresol and p-cresol, with acetone as by-product. But the complexity of this method is much higher than the synthesis of phenol. The product obtained from this method comprises hardly any o-cresol with the rate of m-cresol to p-cresol is approximate 7:3. It is the main process route for the m-cresol synthesis in the world. The purity of the product obtained from this method is high. It is suitable for production on a large scale. There are disadvantages of extremely technique difficult, long process and expensive distillation cost.

Presently, many articles and patents focus on the alkylation of phenol with methanol on the metal oxide catalysts. The main product is o-cresol with dimethyl phenol as by-product, without the high value-added p-cresol in the product. The reports about methyl cresol production by alkylation of benzene with phenol on the molecular sieve catalyst are less. The reaction performance of phenol and methanol on Beta Zeolite had been reported in *Chinese Journal of Catalysis*, 1998, 19 (5): 423-427. The stability of the catalyst modified by magnesium, manganese and lanthanum was low. It had been reported in *Chinese Journal of catalysis*, 2001, 22 (6):545-549 that the HZSM-5 catalyst modified by $P_2O_5$, MgO and $Sb_2O_3$ could improve the selectivity of aromatic ether and reduce the selectivity of cresol and dimethyl phenol. O-cresol selectivity increases with the increase of oxide loading amount. The appropriate oxide modification could improve the selectivity of p-cresol. After phosphorus modification, the para-selectivity increased to 35.87% and the cresol selectivity decreased to 44.10%. Alkylation of phenol with methanol on the hydrogen-form zeolite catalyst was reported in *Appl. Catal. A: Gen,* 342 (2008) 40-48, *J. Mol. Catal. A: Chem.,* 327 (2010) 63-72 and *Catalysis Today* 133-135 (2008) 720-728, in which a large amount of nitrogen used as dilution gas, without a value for industrial application due to the harsh reaction condition and low stability of the catalyst. At present, there is no industrial unit for cresol production via gas phase alkylation of phenol with methanol using the molecular sieve as the catalyst. In traditional industrial production process of cresol, the usage of strong acid and alkali bring the generation of industrial waste water, the serious pollution to environment and the corrosion to equipment. To develop an industrial technology of cresol production via gas phase alkylation of phenol by using molecular sieve as catalyst is extremely urgent. The present invention aims at providing a method of cresol synthesis by shape alkylation of phenol with methanol, in which phenol and methanol are used as feedstock, modified molecular sieve are used as catalyst, the selectivity of cresol reached 90%, the para-selectivity reached 58%, and the stability of catalyst is good. The catalyst is environmental friendly and non-corrosive to the equipment with a good stability and a broad prospect in industrial application.

DISCLOSURE

The technical problems to be solved in the present invention are the corrosion of equipment and the generation of a lot of waste water in previous p-cresol production technologies. The present invention provides a method for producing cresol from phenol and methanol by a shape selective catalysis. Using phenol and methanol as feedstock, cresol is high selectively produced by gas phase alkylation on molecular sieve catalyst, without the corrosion of equipment and the generation of a lot of waste water. The method in the present invention is environmental friendly with a broad prospect in industrial application.

To solve the above problems, the scheme used in the present invention is as follows: a method for producing cresol from phenol and methanol via gas phase alkylation, in which phenol and methanol are preheated and mixed with a diluent gas, then continuously going through a catalyst bed comprising the catalyst for alkylation of phenol with methanol, to produce cresol by gas phase reaction at the reaction temperature from 200° C. to 500° C. and the weight hourly space velocity from $0.5\ h^{-1}$ to $20\ h^{-1}$; wherein the preparation of said catalyst comprise a forming step by mixing a binder with an active component consisted of molecular sieve, and a modification step by using at least one of an acid, a silanization reagent or a steam treatment to adjust the acid sites.

In the method of the present invention, the preparation of said catalyst comprises an oxide modification step.

In the method of the present invention, the weight percentage of the molecular sieve in said catalyst is at a range from 60 wt % to 85 wt %, and the weight percentage of the binder in said catalyst is at a range from 15 wt % to 40 wt %; wherein the molecular sieve is hydrogen form or ammonium form. Said binder is neutral oxide and said binder is at least one selected from silica sol, diatomite or silica. Said molecular sieve is at least one selected from ZSM-5 zeolite, MCM-22 zeolite or Beta zeolite, and the molar ratio of silicon to aluminum in said molecular sieve is from 20 to 80.

The method for producing cresol from phenol and methanol via gas phase alkylation in the present invention is usually conducted at atmospheric pressure.

In the method for producing cresol from phenol and methanol via gas phase alkylation of the present invention, the preparation of said catalyst for alkylation of phenol with methanol comprises steps of: (1) a extrusion forming step carried out by mixing a binder with molecular sieve, then drying and calcinating at a temperature range from 550° C. to 700° C. for a time range from 4 hours to 10 hours; (2) a modification step conducted by using an acid, then drying and calcinating at a temperature range from 500° C. to 600° C. for a time range from 2 hours to 10 hours; (3) a modification step conducted by using a silanization reagent, then drying and calcinating at a temperature range from 500° C. to 800° C. for a time range from 2 hours to 10 hours; (4) an oxide modification step, then drying and calcinating at a temperature range from 550° C. to 700° C. for a time range from 3 hours to 10 hours; (5) a modification step conducted by using an aqueous vapor with the temperature range from 350° C. to 800° C. for a time range from 0.5 hours to 10 hours.

In the method of the present invention, the acid is selected from inorganic acid and organic acid; wherein the inorganic acid is diluted nitric acid or boric acid, and the organic acid is oxalic acid or citric acid. Said modification step by using an acid is conducted by impregnating catalyst with diluted nitric acid or boric acid at room temperature for a time range from 4 hours 24 hours, or conducted by impregnating catalyst with oxalic acid or citric acid at 80° C. for a time range from 4 hours to 12 hours.

In the method of the present invention, an incipient-wetness impregnation method is used in said modification step by using a silanization reagent. The silanization reagent is at least one selected from tetraethoxysilane, phenyl methyl silicone oil or dimethyl silicone oil. The impregnation process is conducted for a time range from 2 hours to 10 hours, and the solvent is cyclohexane or n-hexane.

In the method of the present invention, said oxide of the oxide modification step is at least one selected from alkaline earth metal oxide, transition metal oxide and phosphorus oxide. Said alkaline earth metal oxide is calcium oxide or barium oxide, and the weight percentage of said alkaline earth metal oxide in the catalyst is from 0.1% to 10%; wherein said transition metal oxide is ferric oxide or nickel oxide, and the weight percentage of said transition metal oxide in the catalyst is from 0.1% to 10%; wherein said phosphorus oxide is from diammonium phosphate or ammonium dihydrogen phosphate, and the weight percentage of $P_2O_5$ in the catalyst is from 0.01% to 3%.

In the method of the present invention, in said modification step by using a steam, the steam is 100% aqueous vapor, and the modification temperature is from 350° C. to 800° C., and the modification time is from 0.5 to 10 hours.

In the method of the present invention, said diluent gas is $N_2$ or aqueous vapor, and the molar ratio of the diluent gas to phenol is from 0.5 to 20.

Herein, the further explanation is that in the preparation of catalyst, the modification step and the proportion of the modification agents in catalyst are optimized and controlled according to the structural characteristics and the quantity of acid sites on inner and outer surface of molecular sieves; and in the forming step, the binder is selected from silica sol, diatomite or silica, resulting in the increase of silicon hydroxyls on the surface of molecular sieves after calcination. Conducting the acid modification step behind the forming step is beneficial for increasing the efficiency of silanization. The silanization modification can eliminate the external surface acidity and narrowing the pore opening of the molecular sieve to improve the para-selectivity. The phosphorus oxide modification is to further eliminate the external surface acidity of the molecular sieve and enhance the hydrothermal stability of catalyst. The steam modification is to enhance the hydrothermal stability of catalyst. The synergy of above modification processes resulted in excellent para-selectivity and intensity enough to meet the requirement of industrial application.

In the preparation of catalyst, the forming step uses spray drying method or extrusion molding method after mixing the molecular sieve, binder and water. The molecular sieve is hydrogen form or ammonium form of ZSM-5 zeolite, MCM-22 zeolite or Beta zeolite. Formed molecular sieve obtained in the forming step is treated by the acid, by impregnating the formed molecular sieve in nitric acid or boric acid at room temperature for a time range from 4 hours to 24 hours, or by impregnating the formed molecular sieve in oxalic acid or citric acid at 80° C. for a time range from 4 hours to 12 hours. According to the difference of the external surface of the molecular sieve, the modification step by using silanization reagent need to be conducted one or two times. And the silanization reagent is phenyl methyl silicone oil or dimethyl silicone oil dissolving in n-hexane or cyclohexane. Said phosphorus oxide in the phosphorus oxide modification is diammonium phosphate or ammonium dihydrogen phosphate and the weight percentage of $P_2O_5$ in the catalyst is from 0.8% to 3.0%. In said catalyst modification step by using a steam, the steam is 100% aqueous vapor, and the modification temperature is from 350° C. to 800° C., and the modification time is from 0.5 to 10 hours.

According to the difference of forming method, the catalyst can be used as fluidized bed catalyst or fixed bed catalyst. Fluidized bed catalyst is prepared by above modification steps after the spray forming. Fixed bed catalyst is prepared by above modification steps after the extrusion molding.

It needs to be explained that the modification method is chosen according to the acid strength and the density of different acid sites in the molecular sieve, and various modified methods are used to obtain the target catalyst in the present invention. For the molecular sieve in the catalyst with small density of acid sites, a desired density of acid sites can be obtained by using one or two modified methods in the present invention. Therefore, the modification step by using only one of modification reagent is also covered by the present invention. For example, the modification steps comprising only calcium oxide modification, or only phosphorus oxide modification, or only silanization modification, or only steam modification are all covered by the present invention.

The MCM-22 zeolite in examples is synthesized according to the method in U.S. Pat. No. 4,954,325.

Using sodium aluminate as aluminium source, silica sol for silicon source, sodium hydroxide as alkaline source, cycloheximide (HMI) as template, the molar ratio in the synthetic liquid is: $SiO_2/Al_2O_3$=R, $OH^-/SiO_2$=0.18, $Na/SiO_2$=0.18, $HMI/SiO_2$=0.35, $H_2O/SiO_2$=44.9; and the synthesis is conducted with the rotate crystallization at 150° C. for 168 hours. Wherein, the value of R can be adjusted according to the different ratios of aluminum to silicon in the target molecular sieve.

The ZSM-5 zeolite is produced by Nankai University catalyst factory, the product name is NKF-5. The Beta zeolite is produced by Nankai University catalyst factory, the product name is NKF-6.

EXAMPLES

The present invention will be described in details by the following examples.

Example 1

Preparation process of the catalyst were as following steps: 120 g of ZSM-5 zeolite with the molar ratio of Si/Al=20 was mixed with 60 g of diatomite and 100 g of silica sol containing 20 wt % of silicon dioxide, into which appropriate amount of dilute nitric acid with the mass concentration of 10% was added as an auxiliaries and the mixture was formed by extrusion forming method. After being dried at 120° C., calcinated at 500° C. for 10 hours and cut, the columnar catalyst matrix A0 with height of 1 mm to 3 mm was obtained. 20 g of catalyst matrix A0 was added into 50 ml of nitric acid solution with the mass concentration of 10%, impregnated at room temperature for 4 hours. After being dried at 120° C. and calcinated at 500° C. for 10 hours, A1 was obtained. 20 g of A1 was added into 7.5 g of a cyclohexane solution of phenyl methyl silicone oil with the mass concentration of 50%, impregnated at room temperature for 2 hours. After being dried at 120° C. and calcinated at 500° C. for 2 hours, A2 was obtained. 20 g of A2 was added into an aqueous solution of ammonium dihydrogen phosphate, impregnated at room temperature for 12 hours. After being dried at 120° C. and calcinated at 700° C. for 3 hours, A3 with the weight percentage of $P_2O_5$ of 3% was obtained. 20 g of A3 was treated in 100% aqueous vapor for 10 hours at the temperature of 350° C. After being calcinated at 550° C. for 3 hours, the catalyst A was obtained. The weight percentage of ZSM-5 zeolite in the catalyst A was 60%.

Example 2

Preparation process of the catalyst were as following steps: 170 g of ZSM-5 zeolite with the molar ratio of Si/Al=30 was mixed with 100 g of silica sol containing 30 wt % of silicon dioxide, into which appropriate amount of dilute nitric acid with the mass concentration of 10% was added as an auxiliaries and the mixture was formed by extrusion forming method. After being dried at 120° C., calcinated at 700° C. for 4 hours and cut, the columnar catalyst matrix B0 with height of 1 mm to 3 mm was obtained. 20 g of catalyst matrix B0 was added into 50 ml of ammonium nitrate solution with the mass concentration of 10%, impregnated at room temperature for 10 hours. After being dried at 120° C. and calcinated at 600° C. for 2 hours, B1 was obtained. 20 g of B1 was added into 7.5 g of a cyclohexane solution of phenyl methyl silicone oil with the mass concentration of 50%, impregnated at room temperature for 24 hours. After being dried at 120° C. and calcinated at 800° C. for 2 hours, B2 was obtained. 20 g of B2 was added into an aqueous solution of ammonium dihydrogen phosphate, impregnated at room temperature for 12 hours. After being dried at 120° C. and calcinated at 550° C. for 10 hours, B3 with the weight percentage of $P_2O_5$ of 0.01% was obtained. 20 g of B3 was treated in 100% aqueous vapor for 0.5 hours at the temperature of 800° C. After being calcinated at 550° C. for 3 hours, the catalyst B was obtained. The weight percentage of ZSM-5 zeolite in the catalyst B was 85%.

Example 3

Preparation process of the catalyst were as following steps: 200 g of ZSM-5 zeolite with the molar ratio of Si/Al=400 was mixed with 20 g of diatomite and 100 g of silica sol containing 30 wt % of silicon dioxide, into which appropriate amount of dilute nitric acid with the mass concentration of 10% was added as an auxiliaries and the mixture was formed by extrusion forming method. After being dried at 120° C., calcinated at 550° C. for 4 hours and cut, the columnar catalyst matrix D0 with height of 1 mm to 3 mm was obtained. 20 g of catalyst matrix D0 was added into 50 ml of nitric acid solution with the mass concentration of 10%, impregnated at room temperature for 24 hours. After being dried at 120° C. and calcinated at 600° C. for 3 hours, D1 was obtained. 20 g of D1 was added into 7.5 g of a cyclohexane solution of phenyl methyl silicone oil with the mass concentration of 50%, impregnated at room temperature for 24 hours. After being dried at 120° C. and calcinated at 500° C. for 3 hours, D21 was obtained. 20 g of D21 was added into 7.5 g of an n-hexane solution of dimethyl silicone oil with the mass concentration of 50%, impregnated at room temperature for 10 hours. After being dried at 120° C. and calcinated at 550° C. for 3 hours, D2 was obtained. 20 g of D2 was added into an aqueous solution of calcium nitrate, impregnated at room temperature for 24 hours. After being dried at 120° C. and calcinated at 600° C. for 3 hours, D3 with the weight percentage of calcium oxide of 0.1% was obtained. 20 g of D3 was treated in 100% aqueous vapor for 10 hours at the temperature of 350° C. After being calcinated at 550° C. for 3 hours, the catalyst D was obtained. The weight percentage of ZSM-5 zeolite in the catalyst D was 80%.

Example 4

Preparation process of the catalyst were as following steps: 200 g of ammonium form ZSM-5 zeolite with the molar ratio of Si/Al=30 was mixed with 10 g of diatomite and 100 g of silica sol containing 40 wt % of silicon dioxide, into which appropriate amount of dilute nitric acid with the mass concentration of 10% was added as an auxiliaries and the mixture was formed by extrusion forming method. After being dried at 120° C., calcinated at 550° C. for 4 hours and cut, the columnar catalyst matrix F0 with height of 1 mm to 3 mm was obtained. 20 g of catalyst matrix F0 was added into 150 ml of oxalic acid solution with the concentration of 0.5 mol/L, impregnated at 80° C. for 4 hours. After being dried at 120° C. and calcinated at 500° C. for 2 hours, F1 was obtained. 20 g of F1 was added into 7.5 g of a cyclohexane solution of phenyl methyl silicone oil with the mass concentration of 50%, impregnated at room temperature for 2 hours. After being dried at 120° C. and calcinated at 600° C. for 3 hours, F2 was obtained. 20 g of F2 was added into an aqueous solution of calcium nitrate, impregnated at room temperature for 24 hours. After being dried at 120° C. and calcinated at 700° C. for 3 hours, F3 with the weight percentage of calcium oxide of 10% was obtained. 20 g of F3 was treated in 100% aqueous vapor for 10 hours at the temperature of 350° C. After being calcinated at 550° C. for 3 hours, the catalyst F was obtained. The weight percentage of ZSM-5 zeolite in the catalyst F was 80%.

Example 5

Preparation process of the catalyst were as following steps: 200 g of ammonium form ZSM-5 zeolite with the molar ratio of Si/Al=40 was mixed with 125 g of silica sol containing 40 wt % of silicon dioxide, into which appropriate amount of dilute nitric acid with the mass concentration of 10% was added as an auxiliaries and the mixture was formed by extrusion forming method. After being dried at 120° C., calcinated at 550° C. for 4 hours and cut, the columnar catalyst matrix G0 with height of 1 mm to 3 mm was obtained. 20 g of catalyst matrix G0 was added into 50 ml of oxalic acid solution with the concentration of 0.5 mol/L, impregnated at 80° C. for 12 hours. After being dried at 120° C. and calcinated at 500° C. for 2 hours, G1 was obtained. 20 g of G1 was added into 7.5 g of an n-hexane solution of phenyl methyl silicone oil with the mass concentration of 50%, impregnated at room temperature for 2 hours. After being dried at 120° C. and calcinated at 500° C. for 3 hours, G2 was obtained. 20 g of G2 was added into an aqueous solution of barium nitrate, impregnated at room temperature for 36 hours. After being dried at 120° C. and calcinated at 700° C. for 3 hours, G3 with the weight percentage of barium oxide of 10% was obtained. 20 g of G3 was treated in 100% aqueous vapor for 10 hours at the temperature of 450° C. After being calcinated at 550° C. for 3 hours, the catalyst G was obtained. The weight percentage of ZSM-5 zeolite in the catalyst G was 80%.

Example 6

Preparation process of the catalyst were as following steps: 140 g of ammonium form ZSM-5 zeolite with the molar ratio of Si/Al=30 was mixed with 20 g silicon dioxide and 100 g of silica sol containing 40 wt % of silicon dioxide, into which appropriate amount of dilute nitric acid with the mass concentration of 10% was added as an auxiliaries and the mixture was formed by extrusion forming method. After being dried at 120° C., calcinated at 550° C. for 4 hours and cut, the columnar catalyst matrix H0 with height of 1 mm to 3 mm was obtained. 20 g of catalyst matrix H0 was added into 150 ml of oxalic acid solution with the concentration of 0.5 mol/L, impregnated at 80° C. for 24 hours. After being dried at 120° C. and calcinated at 500° C. for 2 hours, H1 was obtained. 20 g of H1 was added into 7.5 g of a cyclohexane solution of phenyl methyl silicone oil with the mass concentration of 50%, impregnated at room temperature for 2 hours. After being dried at 120° C. and calcinated at 500° C. for 3 hours, H21 was obtained. 20 g of H21 was added into 7.5 g of a cyclohexane solution of phenyl methyl silicone oil with the mass concentration of 50%, impregnated at room temperature for 2 hours. After being dried at 120° C. and calcinated at 550° C. for 3 hours, H22 was obtained. 20 g of H22 was added into an aqueous solution of barium nitrate, impregnated at room temperature for 20 hours. After being dried at 120° C. and calcinated at 700° C. for 3 hours, H3 with the weight percentage of barium oxide of 0.1% was obtained. 20 g of H3 was treated in 100% aqueous vapor for 4 hours at the temperature of 550° C. After being calcinated at 550° C. for 3 hours, the catalyst H was obtained. The weight percentage of ZSM-5 zeolite in the catalyst H was 70%.

Example 7

Preparation process of the catalyst were as following steps: 170 g of ZSM-5 zeolite with the molar ratio of Si/Al=30 was mixed with 100 g of silica sol containing 30 wt % of silicon dioxide, into which appropriate amount of dilute nitric acid with the mass concentration of 10% was added as an auxiliaries and the mixture was formed by extrusion forming method. After being dried at 120° C., calcinated at 550° C. for 4 hours and cut, the columnar catalyst matrix I0 with height of 1 mm to 3 mm was obtained. 20 g of catalyst matrix I0 was added into 150 ml of citric acid solution with the concentration of 0.5 mol/L, impregnated at 80° C. for 8 hours. After being dried at 120° C. and calcinated at 500° C. for 2 hours, I1 was obtained. 20 g of I1 was added into 7.5 g of a cyclohexane solution of phenyl methyl silicone oil with the mass concentration of 50%, impregnated at room temperature for 2 hours. After being dried at 120° C. and calcinated at 500° C. for 3 hours, I21 was obtained. 20 g of I21 was added into 7.5 g of a cyclohexane solution of phenyl methyl silicone oil with the mass concentration of 50%, impregnated at room temperature for 2 hours. After being dried at 120° C. and calcinated at 550° C. for 3 hours, I22 was obtained. 20 g of I22 was added into an aqueous solution of ferric nitrate, impregnated at room temperature for 20 hours. After being dried at 120° C. and calcinated at 700° C. for 3 hours, I3 with the weight percentage of ferric oxide of 0.1% was obtained. 20 g of I3 was treated in 100% aqueous vapor for 10 hours at the temperature of 350° C. After being calcinated at 550° C. for 3 hours, the catalyst I was obtained. The weight percentage of ZSM-5 zeolite in the catalyst I was 85%.

Example 8

Preparation process of the catalyst were as following steps: 160 g of ZSM-5 zeolite with the molar ratio of Si/Al=20 was mixed with 100 g of silica sol containing 40 wt % of silicon dioxide, into which appropriate amount of dilute nitric acid with the mass concentration of 10% was added as an auxiliaries and the mixture was formed by extrusion forming method. After being dried at 120° C., calcinated at 550° C. for 4 hours and cut, the columnar catalyst matrix J0 with height of 1 mm to 3 mm was obtained. 20 g of catalyst matrix J0 was added into 50 ml of nitric acid solution with the mass concentration of 10%, impregnated at room temperature for 10 hours. After being dried at 120° C. and calcinated at 500° C. for 2 hours, J1 was obtained. 20 g of J1 was added into 7.5 g of a cyclohexane solution of phenyl methyl silicone oil with the mass concentration of 50%, impregnated at room temperature for 2 hours. After being dried at 120° C. and calcinated at 500° C. for 3 hours, J2 was obtained. 20 g of J2 was added into an aqueous solution of ferric nitrate, impregnated at room temperature for 24 hours. After being dried at 120° C. and calcinated at 700° C. for 3 hours, J3 with the weight percentage of ferric oxide of 10% was obtained. 20 g of J3 was treated in 100% aqueous vapor for 4 hours at the temperature of 350° C. After being calcinated at 550° C. for 3 hours, the catalyst J was obtained. The weight percentage of ZSM-5 zeolite in the catalyst I was 80%.

Example 9

Preparation process of the catalyst were as following steps: 160 g of ZSM-5 zeolite with the molar ratio of Si/Al=30 was mixed with 100 g of silica sol containing 40 wt % of silicon dioxide, into which appropriate amount of dilute nitric acid with the mass concentration of 10% was added as an auxiliaries and the mixture was formed by extrusion forming method. After being dried at 120° C., calcinated at 550° C. for 4 hours and cut, the columnar catalyst matrix K0 with height of 1 mm to 3 mm was obtained. 20 g of catalyst matrix K0 was added into 50 ml of nitric acid solution with the mass concentration of 10%, impregnated at room temperature for 10 hours. After being dried at 120° C. and calcinated at 500° C. for 2 hours, K1 was obtained. 20 g of K1 was added into 7.5 g of a cyclohexane solution of phenyl methyl silicone oil with the mass concentration of 50%, impregnated at room temperature for 2 hours. After being dried at 120° C. and calcinated at 500° C. for 3 hours, K21 was obtained. 20 g of K21 was added into 7.5 g of a cyclohexane solution of phenyl methyl silicone oil with the mass concentration of 50%, impregnated at room temperature for 2 hours. After being dried at 120° C. and calcinated at 550° C. for 3 hours, K22 was obtained. 20 g of K22 was added into an aqueous solution of nickel nitrate, impregnated at room temperature for 24 hours. After being dried at 120° C. and calcinated at 600° C. for 3 hours, K3 with the weight percentage of nickel oxide of 0.1% was obtained. 20 g of K3 was treated in 100% aqueous vapor for 4 hours at the temperature of 350° C. After being calcinated at 550° C. for 3 hours, the catalyst K was obtained. The weight percentage of ZSM-5 zeolite in the catalyst K was 80%.

Example 10

Preparation process of the catalyst were as following steps: 160 g of ZSM-5 zeolite with the molar ratio of Si/Al=30 was mixed with 40 g of diatomite, into which appropriate amount of dilute nitric acid with the mass concentration of 10% was added as an auxiliaries and the mixture was formed by extrusion forming method. After being dried at 120° C., calcinated at 550° C. for 4 hours and cut, the columnar catalyst matrix L0 with height of 1 mm to 3 mm was obtained. 20 g of catalyst matrix L0 was added into 50 ml of nitric acid solution with the mass concentration of 10%, impregnated at room temperature for 24 hours. After being dried at 120° C. and calcinated at 500° C. for 2 hours, L1 was obtained. 20 g of L1 was added into 7.5 g of a cyclohexane solution of phenyl methyl silicone oil with the mass concentration of 50%, impregnated at room temperature for 2 hours. After being dried at 120° C. and calcinated at 500° C. for 3 hours, L2 was obtained. 20 g of L2 was added into an aqueous solution of nickel nitrate, impregnated at room temperature for 24 hours. After being dried at 120° C. and calcinated at 600° C. for 3 hours, L3 with the weight percentage of nickel oxide of 10% was obtained. 20 g of L3 was treated in 100% aqueous vapor for 2 hours at the temperature of 600° C. After being calcinated at 550° C. for 3 hours, the catalyst L was obtained. The weight percentage of ZSM-5 zeolite in the catalyst L was 80%.

Example 11

Preparation process of the catalyst were as following steps: 170 g of MCM-22 zeolite with the molar ratio of Si/Al=20 was mixed with 100 g of silica sol containing 30 wt % of silicon dioxide, into which appropriate amount of dilute nitric acid with the mass concentration of 10% was added as an auxiliaries and the mixture was formed by extrusion forming method. After being dried at 120° C., calcinated at 550° C. for 4 hours and cut, the columnar catalyst matrix M0 with height of 1 mm to 3 mm was obtained. 20 g of catalyst matrix M0 was added into 50 ml of nitric acid solution with the mass concentration of 10%, impregnated at room temperature for 24 hours. After being dried at 120° C. and calcinated at 500° C. for 2 hours, M1 was obtained. 20 g of M1 was added into 7.5 g of a cyclohexane solution of phenyl methyl silicone oil with the mass concentration of 50%, impregnated at room temperature for 12 hours. After being dried at 120° C. and calcinated at 500° C. for 3 hours, M2 was obtained. 20 g of M2 was added into an aqueous solution of ammonium dihydrogen phosphate, impregnated at room temperature for 10 hours. After being dried at 120° C. and calcinated at 700° C. for 3 hours, M3 with the weight percentage of $P_2O_5$ of 3% was obtained. 20 g of M3 was treated in 100% aqueous vapor for 10 hours at the temperature of 450° C. After being calcinated at 550° C. for 3 hours, the catalyst M was obtained. The weight percentage of MCM-22 zeolite in the catalyst M was 85%.

Example 12

Preparation process of the catalyst were as following steps: 170 g of MCM-22 zeolite with the molar ratio of Si/Al=60 was mixed with 100 g of silica sol containing 30 wt % of silicon dioxide, into which appropriate amount of dilute nitric acid with the mass concentration of 10% was added as an auxiliaries and the mixture was formed by extrusion forming method. After being dried at 120° C., calcinated at 550° C. for 4 hours and cut, the columnar catalyst matrix N0 with height of 1 mm to 3 mm was obtained. 20 g of catalyst matrix N0 was added into 50 ml of nitric acid solution with the mass concentration of 10%, impregnated at room temperature for 12 hours. After being dried at 120° C. and calcinated at 500° C. for 2 hours, N1 was obtained. 20 g of N1 was added into 7.5 g of a cyclohexane solution of phenyl methyl silicone oil with the mass concentration of 50%, impregnated at room temperature for 2 hours. After being dried at 120° C. and calcinated at 500° C. for 3 hours, N21 was obtained. 20 g of N21 was added into 7.5 g of a cyclohexane solution of phenyl methyl silicone oil with the mass concentration of 50%, impregnated at room temperature for 2 hours. After being dried at 120° C. and calcinated at 550° C. for 3 hours, N22 was obtained. 20 g of N22 was added into an aqueous solution of calcium acetate, impregnated at room temperature for 10 hours. After being dried at 120° C. and calcinated at 650° C. for 3 hours, N3 with the weight percentage of calcium oxide of 3% was obtained. 20 g of N3 was treated in 100% aqueous vapor for 10 hours at the temperature of 350° C. After being calcinated at 550° C. for 3 hours, the catalyst N was obtained. The weight percentage of MCM-22 zeolite in the catalyst N was 85%.

Example 13

Preparation process of the catalyst were as following steps: 170 g of MCM-22 zeolite with the molar ratio of Si/Al=50 was mixed with 100 g of silica sol containing 30 wt % of silicon dioxide, into which appropriate amount of dilute nitric acid with the mass concentration of 10% was added as an auxiliaries and the mixture was formed by extrusion forming method. After being dried at 120° C., calcinated at 550° C. for 4 hours and cut, the columnar catalyst matrix P0 with height of 1 mm to 3 mm was obtained. 20 g of catalyst matrix P0 was added into 50 ml of nitric acid solution with the mass concentration of 10%, impregnated at room temperature for 24 hours. After being dried at 120° C. and calcinated at 500° C. for 2 hours, P1 was obtained. 20 g of P1 was added into 7.5 g of a cyclohexane solution of phenyl methyl silicone oil with the mass concentration of 50%, impregnated at room temperature for 2 hours. After being dried at 120° C. and calcinated at 500° C. for 3 hours, P21 was obtained. 20 g of P21 was added into 7.5 g of a cyclohexane solution of phenyl methyl silicone oil with the mass concentration of 50%, impregnated at room temperature for 2 hours. After being dried at 120° C. and calcinated at 550° C. for 3 hours, P22 was obtained. 20 g of P22 was added into an aqueous solution of barium nitrate, impregnated at room temperature for 36 hours. After being dried at 120° C. and calcinated at 700° C. for 3 hours, P3 with the weight percentage of barium oxide of 3% was obtained. 20 g of P3 was treated in 100% aqueous vapor for 10 hours at the temperature of 350° C. After being calcinated at 550° C. for 3 hours, the catalyst P was obtained. The weight percentage of MCM-22 zeolite in the catalyst P was 85%.

Example 14

Preparation process of the catalyst were as following steps: 160 g of MCM-22 zeolite with the molar ratio of Si/Al=40 was mixed with 20 g of diatomite and 100 g of silica sol containing 20 wt % of silicon dioxide, into which appropriate amount of dilute nitric acid with the mass concentration of 10% was added as an auxiliaries and the mixture was formed by extrusion forming method. After being dried at 120° C., calcinated at 550° C. for 4 hours and cut, the columnar catalyst matrix R0 with height of 1 mm to 3 mm was obtained. 20 g of catalyst matrix R0 was added into 50 ml of nitric acid solution with the mass concentration of 10%, impregnated at room temperature for 10 hours. After being dried at 120° C. and calcinated at 500° C. for 2 hours, R1 was obtained. 20 g of R1 was added into 7.5 g of a cyclohexane solution of phenyl methyl silicone oil with the mass concentration of 50%, impregnated at room temperature for 2 hours. After being dried at 120° C. and calcinated at 500° C. for 3 hours, R2 was obtained. 20 g of R2 was added into an aqueous solution of ferric nitrate, impregnated at room temperature for 20 hours. After being dried at 120° C. and calcinated at 700° C. for 3 hours, P3 with the weight percentage of ferric oxide of 3% was obtained. 20 g of P3 was treated in 100% aqueous vapor for 6 hours at the temperature of 350° C. After being calcinated at 550° C. for 3 hours, the catalyst R was obtained. The weight percentage of MCM-22 zeolite in the catalyst R was 80%.

Example 15

Preparation process of the catalyst were as following steps: 170 g of Beta zeolite with the molar ratio of Si/Al=20 was mixed with 100 mL of silica sol containing 20 wt % of silicon dioxide, into which appropriate amount of dilute nitric acid with the mass concentration of 10% was added as an auxiliaries and the mixture was formed by extrusion forming method. After being dried at 120° C., calcinated at 550° C. for 4 hours and cut, the columnar catalyst matrix S0 with height of 1 mm to 3 mm was obtained. 20 g of catalyst matrix S0 was added into 50 ml of citric acid solution with the concentration of 0.5 mol/L, impregnated at 80° C. for 8 hours. After being dried at 120° C. and calcinated at 500° C. for 2 hours, S1 was obtained. 20 g of 51 was added into 7.5 g of a cyclohexane solution of phenyl methyl silicone oil with the mass concentration of 50%, impregnated at room temperature for 2 hours. After being dried at 120° C. and calcinated at 550° C. for 3 hours, S22 was obtained. 20 g of S22 was added into an aqueous solution of ammonium dihydrogen phosphate, impregnated at room temperature for 20 hours. After being dried at 120° C. and calcinated at 700° C. for 3 hours, S3 with the weight percentage of $P_2O_5$ of 3% was obtained. 20 g of S3 was treated in 100% aqueous vapor for 4 hours at the temperature of 550° C. After being calcinated at 550° C. for 3 hours, the catalyst S was obtained. The weight percentage of Beta zeolite in the catalyst S was 85%.

Example 16

Preparation process of the catalyst were as following steps: 160 g of MCM-22 zeolite with the molar ratio of Si/Al=30 was mixed with 100 g of silica sol containing 40 wt % of silicon dioxide, into which appropriate amount of dilute nitric acid with the mass concentration of 10% was added as an auxiliaries and the mixture was formed by extrusion forming method. After being dried at 120° C., calcinated at 550° C. for 4 hours and cut, the columnar catalyst matrix T0 with height of 1 mm to 3 mm was obtained. 20 g of catalyst matrix T0 was added into 50 ml of boric acid solution with the mass concentration of 2%, impregnated at 80° C. for 24 hours. After being dried at 120° C. and calcinated at 600° C. for 2 hours, the catalyst T was obtained. The weight percentage of MCM-22 zeolite in the catalyst T was 80%.

Example 17

Preparation process of the catalyst were as following steps: 160 g of ZSM-5 zeolite with the molar ratio of Si/Al=60 was mixed with 100 g of silica sol containing 40 wt % of silicon dioxide, into which appropriate amount of dilute nitric acid with the mass concentration of 10% was added as an auxiliaries and the mixture was formed by extrusion forming method. After being dried at 120° C., calcinated at 550° C. for 4 hours and cut, the columnar catalyst matrix U0 with height of 1 mm to 3 mm was obtained. 20 g of catalyst matrix U0 was added into 50 ml of boric acid solution with the mass concentration of 2%, impregnated at 80° C. for 24 hours. After being dried at 120° C. and calcinated at 600° C. for 2 hours, the catalyst U was obtained. The weight percentage of ZSM-5 zeolite in the catalyst U was 80%.

Example 18

Alkylation reaction of phenol with methanol to produce cresol was carried out in a fixed bed reactor on the catalysts obtained in Example 1 to 17, respectively. The feedstock of phenol and methanol mixed with aqueous vapor were introduced into the reactor after being preheated, to produce cresol. The reaction product was analyzed by the on-line chromatography. Gas chromatograph was Agilent 7890A, and the chromatographic column was cyclodextrin column (30 m×0.25 mm×0.25 μm). The analysis condition of the chromatograph was as follows: for the column temperature, initial temperature was 150° C. for 15 minutes, which then rose to 180° C. with a heating rate of 10° C./minute and kept for 5.3 minutes; the carrier gas was high purity nitrogen with the column head pressure of 6.5 psia and flow rate of 12.6 cm/s. The catalyst loading capacity was 6.0 g, and the weight hourly space velocity was $2\ h^{-1}$ to $6\ h^{-1}$. The reaction temperature was 300° C. to 500° C. Aqueous vapor as diluent gas, the molar rate of the diluent gas to phenol was 0.5 to 20. The molar rate of methanol to phenol in feedstocks was 1:1. The results of reacting for 72 hours on each catalyst were shown in Table 1.

Percent conversion of phenol=(Weight percent of phenol in the feedstock−Weight percent of phenol and anisole in reaction product)/Weight percent of phenol in the feedstock×100%

Selectivity of cresol=Weight percent of cresols in reaction product/Percent conversion of phenol×100%

Para-selectivity of cresol=Weight percent of p-cresol in reaction product/Weight percent of cresol in reaction product×100%

TABLE 1

| | Reaction condition and results | | | | | |
|---|---|---|---|---|---|---|
| Catalyst | Reaction temperature (° C.) | Weight hourly space velocity ($h^{-1}$) | Water in diluent gas/phenol (molar rate) | Percent conversion of phenol (%) | Para-selectivity of cresol (%) | Selectivity of cresol (%) |
| A | 450 | 2 | 3 | 20 | 29 | 72 |
| B | 400 | 3 | 5 | 29 | 32 | 85 |
| D | 450 | 3 | 2 | 18 | 30 | 60 |
| F | 500 | 3 | 6 | 25 | 32 | 72 |
| G | 500 | 3 | 10 | 32 | 38 | 87 |
| H | 500 | 2 | 6 | 28 | 30 | 70 |
| I | 200 | 0.5 | 2 | 20 | 30 | 78 |
| J | 300 | 2 | 6 | 24 | 35 | 73 |
| K | 350 | 3 | 6 | 28 | 30 | 70 |
| L | 300 | 3 | 6 | 20 | 30 | 80 |
| M | 300 | 5 | 4 | 28 | 40 | 89 |
| N | 350 | 20 | 0.5 | 15 | 58 | 90 |
| P | 300 | 5 | 6 | 20 | 40 | 87 |
| R | 320 | 2 | 3 | 35 | 42 | 85 |
| S | 280 | 2 | 4 | 30 | 36 | 65 |
| U | 400 | 3 | 6 | 20 | 21 | 80 |
| T | 450 | 3 | 6 | 28 | 20 | 75 |

Example 19 to 22

Evaluating device and analysis method were the same as example 18. The catalyst loading capacity was 20.0 g. The molar rate of methanol to phenol in feedstocks was 1:1. The weight hourly space velocity was $3\ h^{-1}$. The diluent gas is aqueous vapor or nitrogen, and the molar rate of diluent gas to phenol in the feedstock was 6. The results of Example 19 to 22 were shown in Table 2.

TABLE 2

| | Results of Example 19 to 22 | | | | | | |
|---|---|---|---|---|---|---|---|
| Example | Catalyst | Reaction temperature (° C.) | Diluent gas | Raction time (h) | Percent conversion of phenol (%) | Para-selectivity of cresol (%) | Selectivity of cresol (%) |
| 19 | B | 400 | $N_2$ | 500 | 29 | 40 | 90 |
| 20 | F | 450 | aqueous vapor | 600 | 30 | 39 | 85 |
| 21 | M | 320 | $N_2$ | 500 | 28 | 40 | 90 |
| 22 | N | 320 | Aqueous vapor | 600 | 30 | 38 | 87 |

The invention claimed is:

1. A method for producing cresol from phenol and methanol via gas phase alkylation, in which phenol and methanol are preheated and mixed with a diluent gas, then continuously going through a catalyst bed comprising the catalyst for alkylation of phenol with methanol, to produce cresol by gas phase reaction at a reaction temperature from 200° C. to 500° C. and a weight hourly space velocity from 0.5 $h^{-1}$ to 20 $h^{-1}$; wherein the preparation of said catalyst comprise a forming step of mixing a binder with an active component consisting of molecular sieve, and a modification step of using at least one of an acid, a silanization reagent or a steam treatment to adjust the acid sites.

2. A method for producing cresol from phenol and methanol via gas phase alkylation according to claim 1, wherein the preparation of said catalyst comprises an oxide modification step.

3. A method for producing cresol from phenol and methanol via gas phase alkylation according to claim 1, wherein the weight percentage of the molecular sieve in said catalyst is within a range from 60 wt % to 85 wt %, and the weight percentage of the binder in said catalyst is within a range from 15 wt % to 40 wt %.

4. A method for producing cresol from phenol and methanol via gas phase alkylation according to claim 1, wherein the binder is neutral oxide.

5. A method for producing cresol from phenol and methanol via gas phase alkylation according to claim 1, wherein the molecular sieve is at least one selected from ZSM-5 zeolite, MCM-22 zeolite or Beta zeolite, and the molar ratio of silicon to aluminum in the molecular sieve is within the range from 20 to 80.

6. A method for producing cresol from phenol and methanol via gas phase alkylation according to claim 1, wherein the acid is at least one selected from inorganic acid or organic acid; wherein the inorganic acid is diluted nitric acid or boric acid, and the organic acid is oxalic acid or citric acid.

7. A method for producing cresol from phenol and methanol via gas phase alkylation according to claim 1, wherein an incipient-wetness impregnation method is used in said modification step by using a silanization reagent; wherein the silanization reagent is at least one selected from tetraethoxysilane, phenyl methyl silicone oil or dimethyl silicone oil.

8. A method for producing cresol from phenol and methanol via gas phase alkylation according to claim 2, wherein the oxide of the oxide modification step is at least one selected from alkaline earth metal oxide, transition metal oxide or phosphorus oxide.

9. A method for producing cresol from phenol and methanol via gas phase alkylation according to claim 8, wherein said alkaline earth metal oxide is calcium oxide or barium oxide; wherein said transition metal oxide is ferric oxide or nickel oxide; wherein said phosphorus oxide is diammonium phosphate or ammonium dihydrogen phosphate.

10. A method for producing cresol from phenol and methanol via gas phase alkylation according to claim 1, wherein in said modification step is a steam treatment, the steam is 100% aqueous vapor, the modification temperature is from 350° C. to 800° C. and the modification time is from 0.5 h to 10 h.

11. A method for producing cresol from phenol and methanol via gas phase alkylation according to claim 1, wherein the binder is at least one selected from silica sol, diatomite or silica.

* * * * *